United States Patent
Hara

(10) Patent No.: US 10,463,231 B2
(45) Date of Patent: Nov. 5, 2019

(54) ENDOSCOPE

(71) Applicant: FUJIFILM Corporation, Tokyo (JP)

(72) Inventor: Kazuyoshi Hara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 11 days.

(21) Appl. No.: 14/723,472

(22) Filed: May 28, 2015

(65) Prior Publication Data

US 2016/0089000 A1   Mar. 31, 2016

(30) Foreign Application Priority Data

Sep. 29, 2014   (JP) ................................ 2014-198946

(51) Int. Cl.
*A61B 1/00* (2006.01)
*A61B 1/015* (2006.01)

(52) U.S. Cl.
CPC ...... *A61B 1/00029* (2013.01); *A61B 1/00013* (2013.01); *A61B 1/00016* (2013.01); *A61B 1/00112* (2013.01); *A61B 1/00114* (2013.01); *A61B 1/00121* (2013.01); *A61B 1/015* (2013.01)

(58) Field of Classification Search
CPC ............ A61B 1/00064; A61B 1/00066; A61B 1/00105; A61B 1/00112; A61B 1/00114; A61B 1/00117; A61B 1/00119; A61B 1/00121; A61B 1/00124; A61B 1/00126; A61B 1/00128; A61B 1/126; A61B 1/015; A61B 1/0661; A61B 1/0669; A61B 1/07
USPC ................. 600/110, 109, 152, 156, 158, 160
See application file for complete search history.

(56) References Cited

U.S. PATENT DOCUMENTS

| 6,099,465 A | 8/2000 | Inoue |
| 8,465,330 B2 | 6/2013 | Miyagi et al. |
| 2004/0096355 A1* | 5/2004 | Ishibiki ............ A61B 1/00057 422/26 |

(Continued)

FOREIGN PATENT DOCUMENTS

| CN | 102573607 | 7/2012 |
| JP | H10155740 | 6/1998 |

(Continued)

OTHER PUBLICATIONS

"Office Action of Japan Counterpart Application" with English translation thereof, dated Mar. 31, 2017, p. 1-p. 6.

(Continued)

*Primary Examiner* — Ryan N Henderson
*Assistant Examiner* — Pamela F Wu
(74) *Attorney, Agent, or Firm* — JCIPRNET

(57) ABSTRACT

There is provided an endoscope which can perform non-contact electric power supply and non-contact signal transmission and of which assembly, repair, and maintenance can be easily performed. A power receiving unit, an image signal transmission unit, and an endoscope side signal transmission and reception unit are disposed in the space (hollow structure) of a first connector of an endoscope. The first connector of the endoscope includes a first connector case and a second connector case disposed in order from a side of the second connector, and a division line between the first and second connector cases includes an inclined portion that is inclined with respect to an insertion direction of the first and second connectors.

12 Claims, 7 Drawing Sheets

(56) References Cited

U.S. PATENT DOCUMENTS

| | | | | |
|---|---|---|---|---|
| 2012/0095293 A1* | 4/2012 | Bendele | ............ | A61B 1/00119 |
| | | | | 600/158 |
| 2012/0202385 A1* | 8/2012 | Miyagi | ............ | A61B 1/00124 |
| | | | | 439/626 |
| 2013/0204140 A1* | 8/2013 | Irie | ........................ | A61B 8/445 |
| | | | | 600/459 |
| 2014/0184771 A1* | 7/2014 | Mazzetti | ................... | H02J 5/00 |
| | | | | 348/75 |

FOREIGN PATENT DOCUMENTS

| | | |
|---|---|---|
| JP | 2003230621 | 8/2003 |
| JP | 2007135956 | 6/2007 |
| JP | 2013-208187 | 10/2013 |
| WO | 2011052408 | 5/2011 |

OTHER PUBLICATIONS

"Office Action of Japan Counterpart Application" with English translation thereof, dated Dec. 2, 2016, p. 1-p. 7.
"Office Action of China Counterpart Application," dated Sep. 1, 2017, with English translation thereof, p. 1-p. 12.

\* cited by examiner

ENDOSCOPE

CROSS-REFERENCE TO RELATED APPLICATIONS

The present application claims priority under 35 U.S.C. § 119 to Japanese Patent Application No. 2014-198946, filed on Sep. 29, 2014. The above application is hereby expressly incorporated by reference, in its entirety, into the present application.

BACKGROUND OF THE INVENTION

1. Field of the Invention

The present invention relates to an endoscope.

2. Description of the Related Art

An endoscope system is configured to include an endoscope and an endoscope processor device. The endoscope includes an image pick-up unit, such as a charge coupled device (CCD) image sensor to image the inside of a body cavity, and a first connector provided at the end of a universal cord. The endoscope processor device includes a second connector to which the first connector of the endoscope is detachably connected, a control unit for performing image processing and the like on image data output from the endoscope, and a light source. In the endoscope system, the supply of electric power from the endoscope processor device to the endoscope or the transmission of an image signal or a control signal between the endoscope processor device and the endoscope is performed by connecting the first connector of the endoscope and the second connector of the endoscope processor device to each other at an electric contact.

In the endoscope system, it is necessary to perform cleaning and disinfection for the endoscope after use. Therefore, it is necessary to attach a waterproof cap for protecting the electric contact to the first connector of the endoscope. However, not only does it take time and effort to attach and detach the waterproof cap, but also there is a problem that the electric contact is damaged when the attachment of the waterproof cap is forgotten.

In order to respond to such a problem, JP2013-208187A discloses an endoscope system that includes a wireless transmission unit and a wireless receiving unit and a power transmission unit and a power receiving unit in order to perform wireless communication of an image signal and the supply of electric power to an LED light source between an endoscope and an endoscope processor device.

SUMMARY OF THE INVENTION

As described above, in order to perform the supply of electric power and the transmission of a signal in a non-contact manner, it is necessary to arrange devices for transmitting and receiving a control signal or an image signal and devices for supplying and receiving electric power in the first connector of the endoscope and the second connector of the endoscope processor device.

Therefore, the device for transmitting and receiving the control signal, the device for transmitting the image signal, and the device for supplying and receiving electric power are disposed on a side in the first connector of the endoscope that is connected to the second connector of the endoscope processor device. In general, cables from these devices and signal cables, such as a switch cable and a signal cable from the universal cord, are electrically connected to a relay board.

For this reason, at the time of assembly or repair of the first connector of the endoscope, it is necessary to work in a state accessible to the relay board and the cables from the devices and the universal cord. At the time of working in a state where the relay board is completely exposed, that is, when the relay board is taken out to the outside from the first connector, the cables from the devices and the universal cord need to have extra length. Therefore, it is necessary to work while paying attention to the extra length of all cables when returning the relay board to the first connector. For this reason, workability is poor, and space for processing the extra length is required. In addition, since the length of a cable connected to an image communication device is increased, noise is easily generated.

An air and water supply connector, a suction connector, and the like are provided in the first connector of the endoscope. At the time of assembly, repair, and maintenance of the first connector of the endoscope, it is necessary to connect these connectors to a conduit or the like from the universal cord or to remove these connectors from the channel or the like from the universal cord.

The invention has been made in view of such a situation, and it is an object of the present invention to provide an endoscope which can perform non-contact electric power supply and non-contact signal transmission and whose assembly, repair, and maintenance are easy.

An endoscope of the invention includes: an image pick-up unit provided in a distal portion; a light guide for transmitting light to the distal portion; and a first connector that is connected to a second connector of an endoscope processor device and that performs electric power reception, control signal communication, and image signal communication in a non-contact manner between the endoscope and the endoscope processor device in order to drive the image pick-up unit. The first connector has a hollow structure determining an internal space and includes a power receiving unit that receives electric power from a power supply unit in a non-contact manner, an image signal transmission unit that transmits an image signal of the image pick-up unit in a non-contact manner, and an endoscope side signal transmission and reception unit that transmits and receives a control signal for controlling the image pick-up unit in a non-contact manner, the power receiving unit, the image signal transmission unit, and the endoscope side signal transmission and reception unit being disposed in the hollow structure. The first connector includes a first connector case and a second connector case disposed in order from a side of the second connector. A division line between the first and second connector cases includes an inclined portion that is inclined with respect to an insertion direction of the first and second connectors.

Preferably, the division line includes a vertical portion that is perpendicular to the insertion direction.

Preferably, an air and water supply connector and a suction connector are disposed on one side of the first connector case, the power receiving unit, the image signal transmission unit, and the endoscope side signal transmission and reception unit are disposed in the hollow structure on the other side of the first connector case, and the inclined portion of the division line becomes closer to the second connector toward the other side from the one side.

Preferably, the second connector case includes at least one of an auxiliary water supply connector and a balloon connector.

Preferably, the second connector case has at least one of a ventilation connector and an S connector.

Preferably, the first connector comprises a third connector case disposed on an opposite side to the first connector case with respect to the second connector case, and the third connector case has at least one of an S connector and a ventilation connector.

Preferably, the first connector includes a reduced diameter portion toward the other side from one side of the second connector.

Preferably, the division line is formed so as to be closer to the second connector than the reduced diameter portion is.

Preferably, the power supply unit is a primary coil connected to a power source, and the power receiving unit is a secondary coil electromagnetically coupled to the primary coil.

Preferably, the power receiving unit is disposed so as to be closer to the second connector than the image signal transmission unit and the endoscope side signal transmission and reception unit.

It is preferable to further include a circuit board on which the image signal transmission unit and the endoscope side signal transmission and reception unit are mounted.

According to the invention, it is possible to perform non-contact electric power supply and non-contact signal transmission and to easily perform assembly, repair, and maintenance.

DESCRIPTION OF THE PREFERRED EMBODIMENTS

Figure 1:
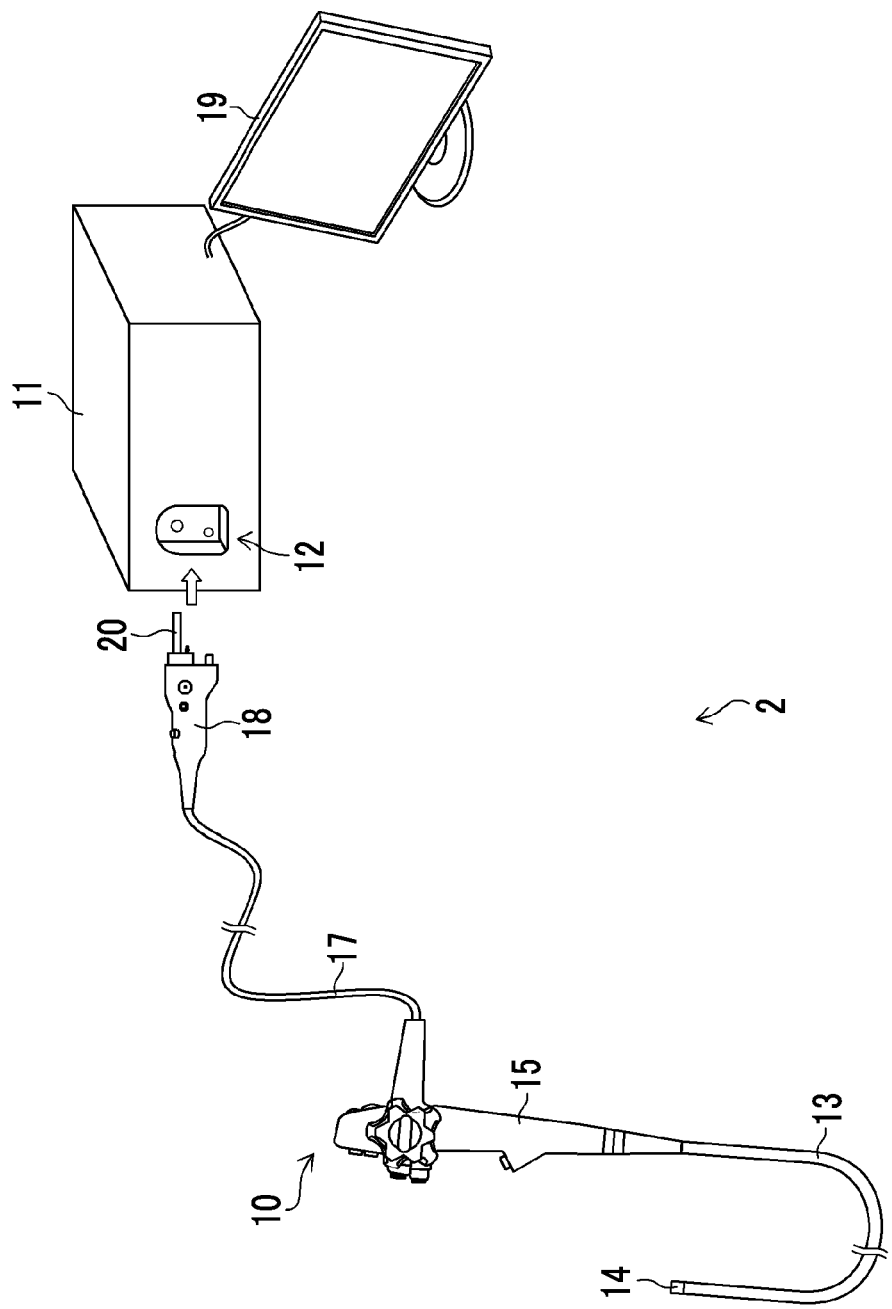
FIG. 1 is an external view showing an endoscope system.

Hereinafter, a preferred embodiment of the invention will be described with reference to the accompanying diagrams. The invention will be described by way of the following preferred embodiment. It is possible to make changes through a number of techniques without departing from the scope of the present invention, and it is possible to use embodiments other than the present embodiment. Accordingly, all changes within the range of the invention are included in the range of the invention.

Here, portions denoted by the same reference numerals in diagrams are the same elements having the same functions. In this specification, when a numerical range is expressed using "~", the values of the upper and lower limits indicated by "~" are assumed to be included in the numerical range.

FIG. 1 is an external view showing an endoscope system to which the invention is applied.

As shown in FIG. 1, an endoscope system 2 includes an endoscope 10 and an endoscope processor device 11.

The endoscope 10 is an example of a flexible endoscope, and includes a flexible insertion part 13 to be inserted into the body cavity of a patient, an operating unit 15 disposed at the proximal end of the insertion part 13, a universal cord 17 disposed in the operating unit 15, and a first connector 18 that is provided at the end of the universal cord 17 and is connected to a second connector 12 of the endoscope processor device 11. However, the endoscope 10 is not limited to the flexible endoscope, and the invention can also be applied to other types of endoscopes, such as a rigid endoscope.

An observation window, an illumination window, and the like are provided on the distal surface of the insertion part 13. An objective optical system that forms subject light from a part to be observed, which is acquired through the observation window, as an optical image, an image pick-up unit that converts the optical image formed by the objective optical system into an electrical signal, and the like are disposed in a distal portion 14 that forms the distal end of the insertion part 13.

The image signal output from the image pick-up unit is transmitted to an image signal transmission unit through a transmission cable that is disposed so as to be inserted into the first connector 18 through the inside of the insertion part 13, the operating unit 15, and the universal cord 17. The image signal is converted into a light signal by the image signal transmission unit, and is optically transmitted to the endoscope processor device 11 in a non-contact manner.

In addition, a light exit part of a light guide to transmit light, which is to be emitted to a part to be observed through the illumination window, is disposed in the distal portion 14. The light guide is disposed so as to be inserted into the first connector 18 through the inside of the insertion part 13, the operating unit 15, and the universal cord 17. A light guide rod 20 connected to the light guide protrudes from the first connector 18.

An angle knob for adjusting the direction of the distal surface of the insertion part 13 in vertical and horizontal directions, an air and water supply button for ejecting air and water from the distal surface of the insertion part 13, a release button for recording an endoscope image as a still image, and the like are provided in the operating unit 15. The direction of the distal surface of the insertion part 13 is adjusted by bending a bending portion provided near the proximal side of the distal portion 14.

The universal cord 17 is covered with a flexible outer wall portion having a long tubular shape. The above-described signal cable, light guide, and air and water supply tube, and the like disposed so as to be inserted into a cavity portion inside the insertion part 13 and a cavity portion inside the operating unit 15 are disposed so as to be inserted into the lumen on the inner side of the outer wall portion.

The first connector 18 is connected to the second connector 12 of the endoscope processor device 11. Between the endoscope 10 and the endoscope processor device 11, supply and reception of electric power, transmission and reception of an image signal, and transmission and reception of a control signal are performed in a non-contact manner through the first connector 18 and the second connector 12. Therefore, as will be described later, a power receiving unit for receiving electric power in a non-contact manner, an image signal transmission unit for optically transmitting the image signal of the image pick-up unit in a non-contact manner, and an endoscope side control signal transmission and reception unit for optically transmitting and receiving a control signal to control the image pick-up unit in a non-contact manner are disposed in the first connector 18.

The second connector 12 is provided in the endoscope processor device 11. As described above, the first connector 18 of the endoscope 10 and the second connector 12 of the endoscope processor device 11 are connected to each other.

The endoscope processor device 11 supplies electric power to the endoscope 10, or transmits and receives various signals to and from the endoscope 10.

The endoscope processor device 11 includes a light source. Light from the light source is supplied to the light guide through the light guide rod 20, and the light is transmitted to the distal portion 14 from the light guide.

The endoscope processor device 11 includes a control unit to control the control signal communication and the image signal communication.

A power supply unit for supplying electric power to the power receiving unit of the endoscope 10 in a non-contact manner, an image signal receiving unit for receiving the signal from the image signal transmission unit of the endoscope 10, and a processor device side signal transmission and reception unit for transmitting and receiving the signal from the endoscope side signal transmission and reception unit of the endoscope 10 are disposed in the second connector 12 connected to the first connector 18.

The endoscope processor device 11 includes an input device (not shown; an operating switch, a keyboard, a mouse, and the like). According to the operation of the operator input through the input device, the overall control of the endoscope system 2 is performed.

The endoscope processor device 11 generates image data to form an image (moving image) or still image of a part to be observed by acquiring the image signal output from the image pick-up unit of the distal portion 14 of the endoscope 10 and performing various kinds of signal processing on the acquired image signal. Then, the generated image data is output to a monitor 19 connected through a cable, and the image or the like of the part to be observed is displayed on the monitor 19. In addition, the generated image data is recorded on a recording medium as necessary.

Figure 2:
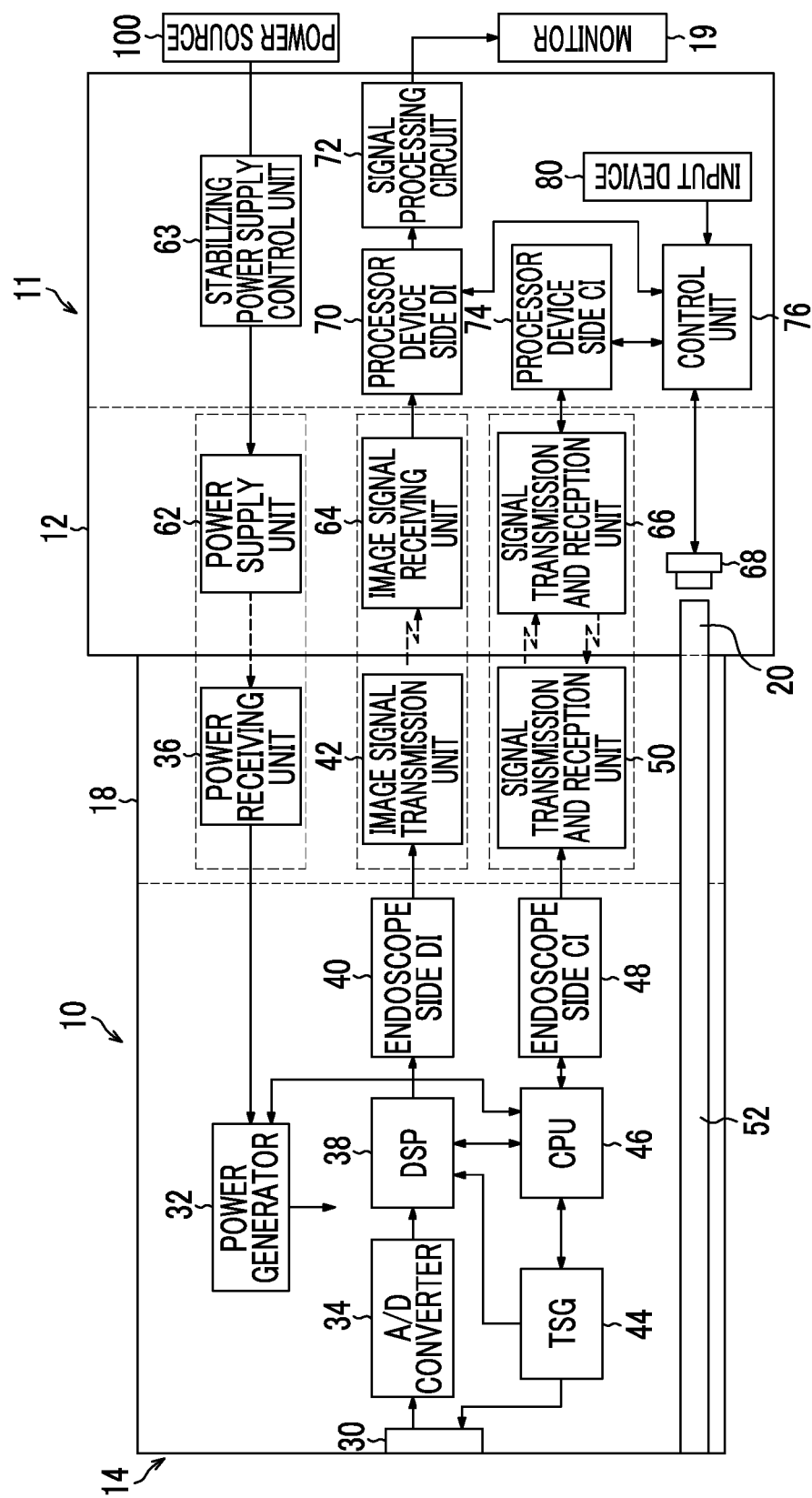
FIG. 2 is a block diagram showing the configuration of the endoscope system.

FIG. 2 is a block diagram showing the configuration of the endoscope system 2 shown in FIG. 1.

The endoscope 10 is detachably connected to the second connector 12 of the endoscope processor device 11 through the first connector 18. In the endoscope system 2 of the present embodiment, the first connector 18 of the endoscope 10 and the second connector 12 of the endoscope processor device 11 are connected to each other, so that the internal circuit of the endoscope 10 and the internal circuit of the endoscope processor device 11 are connected to each other by a non-contact device, such as a transformer or a photocoupler. Therefore, insulation between the internal circuit of the endoscope 10 and the internal circuit of the endoscope processor device 11 is ensured. That is, control signal communication, supply and reception of electric power, and image signal communication can be realized in a non-contact manner.

Electric power required to drive the internal circuit of the endoscope 10 is supplied from the endoscope processor device 11 by non-contact power supply means formed by a power supply unit 62 in the endoscope processor device 11 and a power receiving unit 36 in the endoscope 10. The power receiving unit 36 is disposed in the first connector 18 of the endoscope 10, and the power supply unit 62 is disposed in the second connector 12 of the endoscope processor device 11.

The non-contact power supply means is means for transmitting and receiving electric power in a non-contact manner using electromagnetic coupling. When the first connector 18 of the endoscope 10 is connected to the second connector 12 of the endoscope processor device 11, the power supply unit 62 and the power receiving unit 36 are disposed close to each other so as to be able to be electromagnetically coupled, so that the non-contact transmission of electric power from the power supply unit 62 to the power receiving unit 36 is possible. A commercial power source 100 located outside the endoscope processor device 11 is connected to the power supply unit 62 through a stabilizing power supply control unit 63. Electric power, which is supplied from the commercial power source 100 and is stabilized by the stabilizing power supply control unit 63, is supplied to the power supply unit 62. By the electric power supplied to the power supply unit 62 from the stabilizing power supply control unit 63, non-contact power supply from the power supply unit 62 to the power receiving unit 36 is realized. The power receiving unit 36 receives electric power from the power supply unit 62 in a non-contact manner.

It is preferable that the power supply unit 62 is a primary coil connected to the power source 100 and the power receiving unit 36 is a secondary coil electromagnetically coupled to the primary coil. As the structure of the primary coil and the secondary coil, it is possible to use a structure including a substrate having a plane and a coil wound spirally on the plane.

As the non-contact power supply means, an example in which the power supply unit 62 is a primary coil and the power receiving unit 36 is a secondary coil is shown in the embodiment. However, any means may be used as long as the means can transmit and receive electric power in a non-contact manner.

Here, the electromagnetic coupling means a state in which electric power can be transmitted to the other coil (secondary coil) using a magnetic field generated when a current flows through one coil (primary coil) of two coils.

The endoscope 10 includes a power generator 32 connected to the power receiving unit 36, and the power generator 32 can supply electric power to the internal circuit including an image pick-up unit 30 or the like. For example, the power generator 32 receives a current induced in the power receiving unit 36, and generates control power to be supplied to the internal circuit including the image pick-up unit 30 or a central processing unit (CPU) 46, which will be described later, from the input current. The power generator 32 includes a capacitor that is charged by the current induced in the power receiving unit 36 and a voltage stabilizing circuit that generates a desired voltage from the voltage charged in the capacitor.

The image pick-up unit 30 is disposed in the distal portion 14 of the endoscope 10. The image pick-up unit 30 is a device that converts an optical image of a part to be observed, which is acquired through the observation window and is formed by the objective optical system, into an electrical signal and outputs the electrical signal as an image signal as described above. As the image pick-up unit 30, it is possible to use a solid state image pick-up device, such as a charge coupled device (CCD) image sensor or a complementary metal oxide semiconductor (CMOS) image sensor, for example.

In the present embodiment, transmission and reception of the image signal between the endoscope 10 and the endoscope processor device 11 are performed by non-contact optical communication means. The image signal output from the image pick-up unit 30 is transmitted from the endoscope 10 to the endoscope processor device 11 through the first connector 18 and the second connector 12 by non-contact optical transmission. In the present embodiment, in order to process the image signal from the image pick-up unit 30, an analog/digital (A/D) converter 34, a digital signal processor (DSP) 38, a timing signal generator (TSG) 44, and the like are provided. The image signal from the image pick-up unit 30 is converted into the digital signal from the analog signal by an A/D converter 34. The image signal output from the A/D converter 34 is transmitted to the DSP 38. The DSP 38 performs required processing, such as amplification, gamma correction, and white balance processing, on the image signal from the A/D converter 34.

In order to perform non-contact optical transmission between the endoscope 10 and the endoscope processor device 11, for example, the following configuration is provided. The endoscope 10 includes an endoscope side digital interface (DI) 40 connected to the DSP 38 and an image signal transmission unit 42 connected to the endoscope side DI 40. The image signal processed by the DSP 38 is transmitted to the image signal transmission unit 42 through the endoscope side DI 40. Predetermined processing is performed on the image signal from the image pick-up unit 30, and the light signal is transmitted to the endoscope processor device 11 from the image signal transmission unit 42 according to the processed image signal. The image signal transmission unit 42 may be a light emitting device capable of emitting light for optical communication. For example, a laser light emitting element, a light emitting diode, or the like can be used. The laser light emitting element refers to an element capable of emitting laser light that is coherent light, and it is possible to use a gas laser, a solid state laser, a semiconductor laser, and the like.

At least the image signal transmission unit 42 is disposed in the first connector 18 of the endoscope 10. Other devices, for example, the endoscope side DI 40 and the like may be disposed in the first connector 18 of the endoscope 10.

The endoscope processor device 11 includes an image signal receiving unit 64 that receives a light signal from the image signal transmission unit 42, a processor device side DI 70 connected to the image signal receiving unit 64, and a signal processing circuit 72 connected to the processor device side DI 70. The image signal receiving unit 64 is a light receiving device that converts the received light signal into an electrical signal. For example, a light receiving device of a semiconductor device, such as a photodiode or a phototransistor, can be used. The electrical signal from the image signal receiving unit 64 is output to the monitor 19 through the processor device side DI 70 after being subjected to analog processing by the signal processing circuit 72.

In the present embodiment, image signal transmission and reception means based on non-contact optical communication is formed by the image signal transmission unit 42 and the image signal receiving unit 64. For the image signal transmission unit 42 that transmits the image signal of the image pick-up unit 30 in a non-contact manner and the image signal receiving unit 64 that receives the signal from the image signal transmission unit 42 in a non-contact manner, it is possible to use a wireless communication method and a magnetic communication method without being limited to the non-contact optical communication (optical wireless communication method). The optical wireless communication method refers to a method for transmitting and receiving a signal using infrared rays or the like. The wireless communication method refers to a method for transmitting and receiving a signal by wireless communication (radio waves). The magnetic communication mode refers to a method for transmitting and receiving a signal by providing coils based on a magnetic communication method, generating a modulated signal from the coil on the transmission side as an AC magnetic field, receiving the signal using the coil on the receiving side disposed in the AC magnetic field, and demodulating the signal.

When the first connector 18 of the endoscope 10 is connected to the second connector 12 of the endoscope processor device 11, the image signal transmission unit 42 and the image signal receiving unit 64 are disposed close to each other to allow optical communication therebetween, so that the non-contact optical communication between the image signal transmission unit 42 and the image signal receiving unit 64 is possible.

Transmission and reception of the control signal between the endoscope 10 and the endoscope processor device 11 are performed by non-contact optical communication. In order to control the image pick-up unit 30, the TSG 44 and the CPU 46 are connected to the image pick-up unit 30. Each of the TSG 44 and the CPU 46 outputs a driving signal, which is for making the image pick-up unit 30 acquire an image signal, to the image pick-up unit 30. An endoscope side communication interface (CI) 48 and an endoscope side signal transmission and reception unit 50 are connected to the CPU 46. The endoscope side signal transmission and reception unit 50 is a device capable of optically transmitting and receiving the control signal between the endoscope 10 and the endoscope processor device 11 in a non-contact manner, and includes a light emitting device for optically transmitting the control signal to the endoscope processor device 11 as a light signal and a light receiving device for receiving the control signal from the endoscope processor device 11 as a light signal. As the endoscope side signal transmission and reception unit 50, for example, it is possible to use a non-contact optical data communication unit based on infrared data association (IrDA) including an infrared light emitting element that optically transmits a signal (using infrared rays) and a light receiving element (for example, a photodiode or a phototransistor) that optically receives a signal. At least the endoscope side signal transmission and reception unit 50 is disposed in the first connector 18 of the endoscope 10. Other devices, for example, the endoscope side CI 48 and the like may be disposed in the first connector 18 of the endoscope 10.

The endoscope processor device 11 includes a processor device side signal transmission and reception unit 66 that optically transmits and receives a control signal between the endoscope 10 and the endoscope side signal transmission and reception unit 50 in a non-contact manner and a processor device side CI 74 connected to the processor device side signal transmission and reception unit 66. The processor device side signal transmission and reception unit 66 is a device capable of optically transmitting and receiving the control signal between the endoscope 10 and the endoscope processor device 11 in a non-contact manner, and includes a light emitting device for optically transmitting the control signal to the endoscope 10 as a light signal and a light receiving device for receiving the control signal from the endoscope 10 as a light signal. As the processor device side signal transmission and reception unit 66, it is possible to use a non-contact optical data communication unit based on infrared data association (IrDA) that includes an infrared light emitting element for optically transmitting a signal (using infrared rays), which is different from the endoscope side signal transmission and reception unit 50, and a light receiving element (for example, a photodiode or a phototransistor) for optically receiving a signal, which is different from the endoscope side signal transmission and reception unit 50. Generally, the infrared ray refers to an electromagnetic wave having a wavelength of 0.7 μm to 1 mm.

When the first connector 18 of the endoscope 10 is connected to the second connector 12 of the endoscope processor device 11, the endoscope side signal transmission and reception unit 50 and the processor device side signal transmission and reception unit 66 are disposed close to each other to allow optical communication therebetween, so that non-contact optical transmission and reception between the endoscope side signal transmission and reception unit 50 and the processor device side signal transmission and reception unit 66 is possible.

For the endoscope side signal transmission and reception unit 50 that transmits and receives a control signal to control the image pick-up unit 30 in a non-contact manner and the processor device side signal transmission and reception unit 66 that transmits and receives the control signal from the endoscope side signal transmission and reception unit 50 in a non-contact manner, it is possible to use a wireless communication method and a magnetic communication mode without being limited to the non-contact optical communication (optical wireless communication method).

The endoscope processor device 11 includes a light source 68. As the light source 68, it is possible to use a xenon lamp or a semiconductor device, such as a laser diode or a light emitting diode, for example. The endoscope 10 includes a light guide 52. The light guide rod 20 connected to the light guide is provided at the end of the light guide 52. The light guide rod 20 protrudes from the first connector 18, and is connected to the second connector 12 of the endoscope processor device 11. The light source 68 and the light guide rod 20 are aligned, and light from the light source 68 is transmitted to the distal portion 14 through the light guide rod 20 and the light guide 52.

The endoscope processor device 11 includes a control unit 76. The control unit 76 controls the processor device side DI 70 and the like, which form the internal circuit of the endoscope processor device 11, and the light source 68, and controls the entire endoscope system 2 by transmitting a control signal to the CPU 46 and the like that form the internal circuit of the endoscope 10. For example, the endoscope processor device 11 includes an input device 80 (an operating switch, a keyboard, and the like).

A user inputs an instruction for turning ON/OFF of the power source of the endoscope processor device 11 through the input device 80. A control signal based on the instruction input is transmitted to the CPU 46 of the endoscope 10 from the control unit 76 of the endoscope processor device 11 through the non-contact optical communication means formed by the processor device side signal transmission and reception unit 66 and the endoscope side signal transmission and reception unit 50.

A control signal from the CPU 46 is also transmitted to the control unit 76 of the endoscope processor device 11 through the non-contact optical communication means formed by the processor device side signal transmission and reception unit 66 and the endoscope side signal transmission and reception unit 50.

Figure 3:
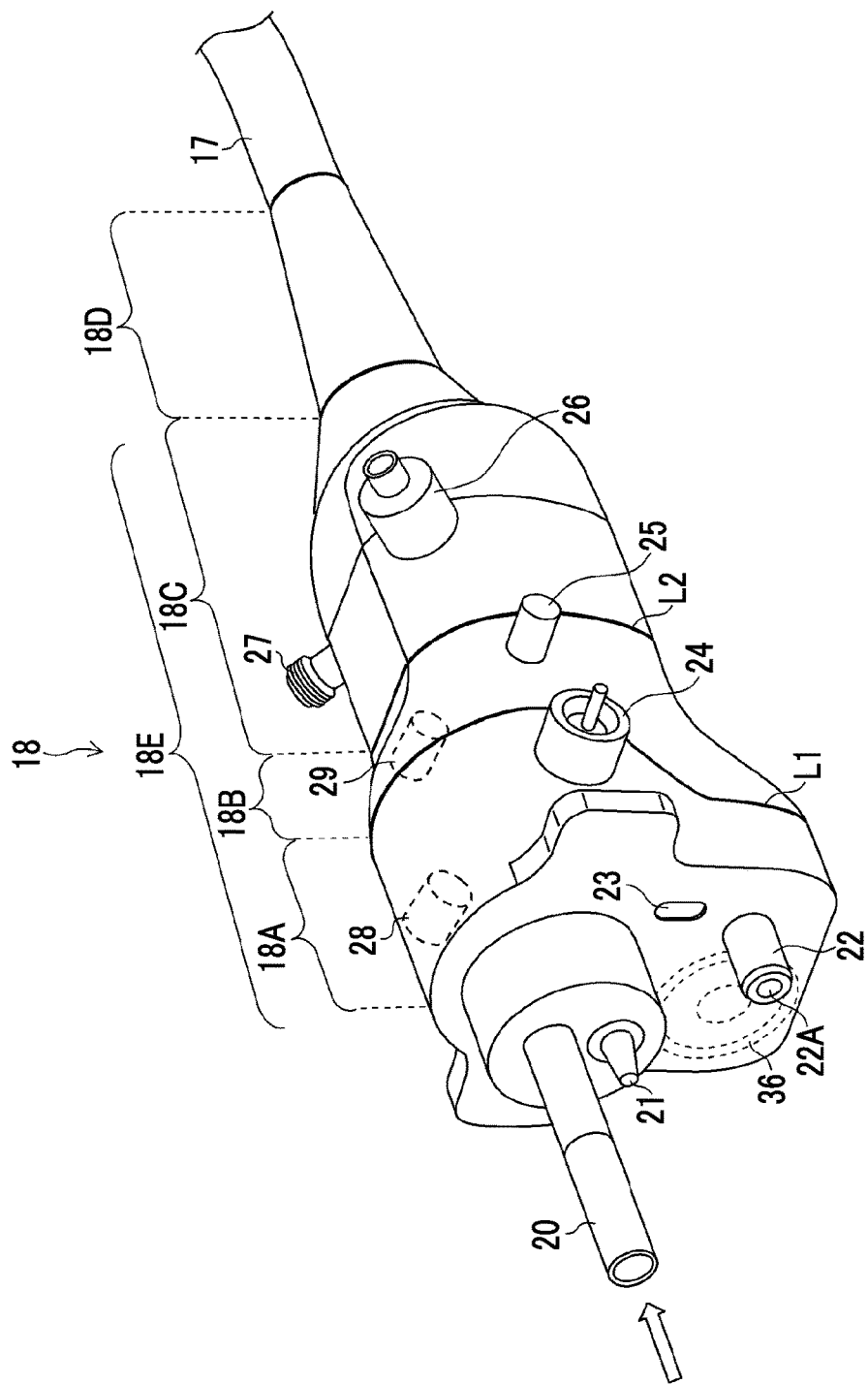
FIG. 3 is an external view of a first connector of an endoscope.

FIG. 3 is an external view of the first connector 18. As described above, supply and reception of electric power, transmission and reception of an image signal, and transmission and reception of a control signal between the endoscope 10 and the endoscope processor device 11 are performed in a non-contact manner. An electric contact directly connected to the endoscope processor device 11 does not need to be provided in the first connector 18.

Accordingly, the first connector 18 can be made to have an electrical insulation property and a waterproof structure covered with a resin having good chemical resistance. By forming the first connector 18 in a waterproof structure, electrical components and the like inside the first connector 18 can be protected against washing water or the like. Accordingly, it is not necessary to attach a separate waterproof cap during the cleaning and disinfection.

As shown in FIG. 3, the first connector 18 includes the light guide rod 20, a shaft 22, and an air cap 21 that protrude toward the second connector 12 (not shown) from the first connector 18.

Since the first connector 18 has a cylindrical shape, the first connector 18 has a hollow structure defining the space therein. The power receiving unit 36, the image signal transmission unit 42, and the endoscope side signal transmission and reception unit 50 described above are disposed in the space (hollow structure) of the first connector 18. The light guide 52 is disposed in the space (hollow structure) of the first connector 18, and the distal portion of the light guide 52 is connected to the light guide rod 20.

As will be described later, conduits, such as an air supply conduit, a water supply conduit, and a suction conduit, are disposed in the space (hollow structure) of the first connector 18.

The first connector 18 of the present embodiment can be configured to include a first connector case 18A, a second connector case 18B, a third connector case 18C, and a cover rubber 18D sequentially from the side connected to the second connector 12 of the endoscope processor device 11.

A first connector body 18E is formed by the first connector case 18A, the second connector case 18B, and the third connector case 18C. A space (hollow structure) is formed in the first connector 18 by the combination of the first connector case 18A, the second connector case 18B, and the third connector case 18C.

The first connector case 18A and the second connector case 18B of the first connector body 18E are separated from each other by a division line L1, and the second connector case 18B and the third connector case 18C are separated from each other by a division line L2. In addition, the first connector body 18E and the cover rubber 18D are separated from each other.

Here, the division line L1 means a portion where the first connector case 18A and the second connector case 18B that form the first connector body 18E are in contact with each other, and the division line L2 means a portion where the second connector case 18B and the third connector case 18C are in contact with each other.

The light guide rod 20 protrudes toward the second connector 12 (in an insertion direction) from the first connector case 18A having a connection surface with respect to the second connector 12. Below the light guide rod 20, an air cap 21 is provided so as to be almost parallel to the light guide rod 20. The air cap 21 communicates with an air and water supply conduit disposed in the endoscope 10 in order to supply air and water to the distal portion 14 of the endoscope 10.

The shaft 22 protrudes from the connection surface of the first connector case 18A along the insertion direction with respect to the second connector 12. The shaft 22 is used for alignment between the image signal transmission unit 42 of the endoscope 10 and the image signal receiving unit 64 of the endoscope processor device 11. In particular, the image signal transmission unit 42 is disposed in the extending direction of the central axis of the shaft 22. A window 22A is provided at the distal end of the shaft 22, so that light can be transmitted therethrough. Through the window 22A, optical transmission and reception of image signals between the image signal transmission unit 42 and the image signal receiving unit 64 are performed in a non-contact manner.

On the connection surface of the first connector case 18A, a window 23 is provided at a position corresponding to the endoscope side signal transmission and reception unit 50. Through the window 23, optical transmission and reception of control signals between the endoscope side signal transmission and reception unit 50 and the processor device side signal transmission and reception unit 66 are performed in a non-contact manner.

In the first connector case 18A, the power receiving unit 36 is disposed at a position close to the connection surface of the first connector case 18A. Since the power receiving unit 36 is disposed inside the first connector case 18A, the power receiving unit 36 is not exposed to the outside.

An air and water supply connector 24 is provided on the side surface of the first connector case 18A. The air and water supply connector 24 is connected to a water supply tank (not shown). By operating the air and water supply button of the operating unit 15, air and water can be supplied to the distal portion 14. Dirt on the lens surface of the distal portion 14 is removed by the water supplied to the distal portion 14. In addition, it is possible to expand the patient's lumen or to remove the water droplets on the lens with the air supplied to the distal portion 14.

In addition, a suction connector 28 is disposed on the side surface of the first connector case 18A opposite to the air and water supply connector 24. By connecting a tube to the suction connector, communication with a suction device (not shown) can be made. By operating the suction button of the operating unit 15 in a state in which the suction device is driven, it is possible to suck a lesion or the like through the forceps opening of the distal portion 14.

In the present embodiment, the suction connector is provided on the side surface of the first connector 18 opposite to the image signal transmission unit 42 when the first connector 18 is viewed from the insertion direction (viewed from the direction of the arrow in FIG. 3). That is, the suction connector is disposed on the side surface of the first connector 18 far from the shaft 22. Through the configuration, for example, even if a lesion comes out of the suction connector 28 when the tube is detached from the suction connector 28, it is possible to suppress the contamination of the window 22A of the shaft 22. On the other hand, since the suction connector 28 is disposed on the side surface of the first connector 18 close to the power receiving unit 36, a lesion may be attached through the suction connector 28. Since the region of the first connector 18 where the power receiving unit 36 is disposed is a plane, cleaning such as wiping can be easily performed.

For example, a balloon connector 25 is provided on the side surface of the second connector case 18B. By connecting a tube to the balloon connector 25, it is possible to inflate and deflate a balloon (not shown) provided in the insertion part 13. In the case of the endoscope 10 in which no balloon is provided in the insertion part 13, it is not necessary to provide the balloon connector 25 in the first connector 18.

An auxiliary water supply connector 29 is disposed on the side surface of the second connector case 18B opposite to the balloon connector 25. By connecting a tube to the auxiliary water supply connector 29, it is possible to supply water to the distal portion 14 of the endoscope 10. By the water supplied to the distal portion 14 through the auxiliary water supply connector 29, foreign matter adhering to the body cavity, blood generated during the endoscopic operation, and the like are removed.

It is preferable that the second connector case 18B includes at least one of the balloon connector 25 and the auxiliary water supply connector 29.

A ventilation connector 26 is provided on the side surface of the third connector case 18C. The ventilation connector 26 is used for the leak test to check the air leakage of the insertion part 13. The ventilation connector 26 communicates with the inside of the first connector 18. Since the inside of the first connector 18 communicates with the inside of each of the universal cord 17, the operating unit 15, and the insertion part 13, the ventilation connector 26 communicates with the inside of the insertion part 13.

In addition, an S connector 27 is disposed on the side surface of the third connector case 18C opposite to the ventilation connector 26. The S connector 27 is a terminal for connection with an S cord for returning a high-frequency current, which leaks to the endoscope 10 when using an electrosurgical device (electric scalpel), to the control unit of the electrosurgical device, for example.

It is preferable that the third connector case 18C includes at least one of the ventilation connector 26 and the S connector 27.

The cover rubber 18D is disposed so as to cover the end of the third connector case 18C. The universal cord 17 protrudes from the cover rubber 18D.

Figure 4:
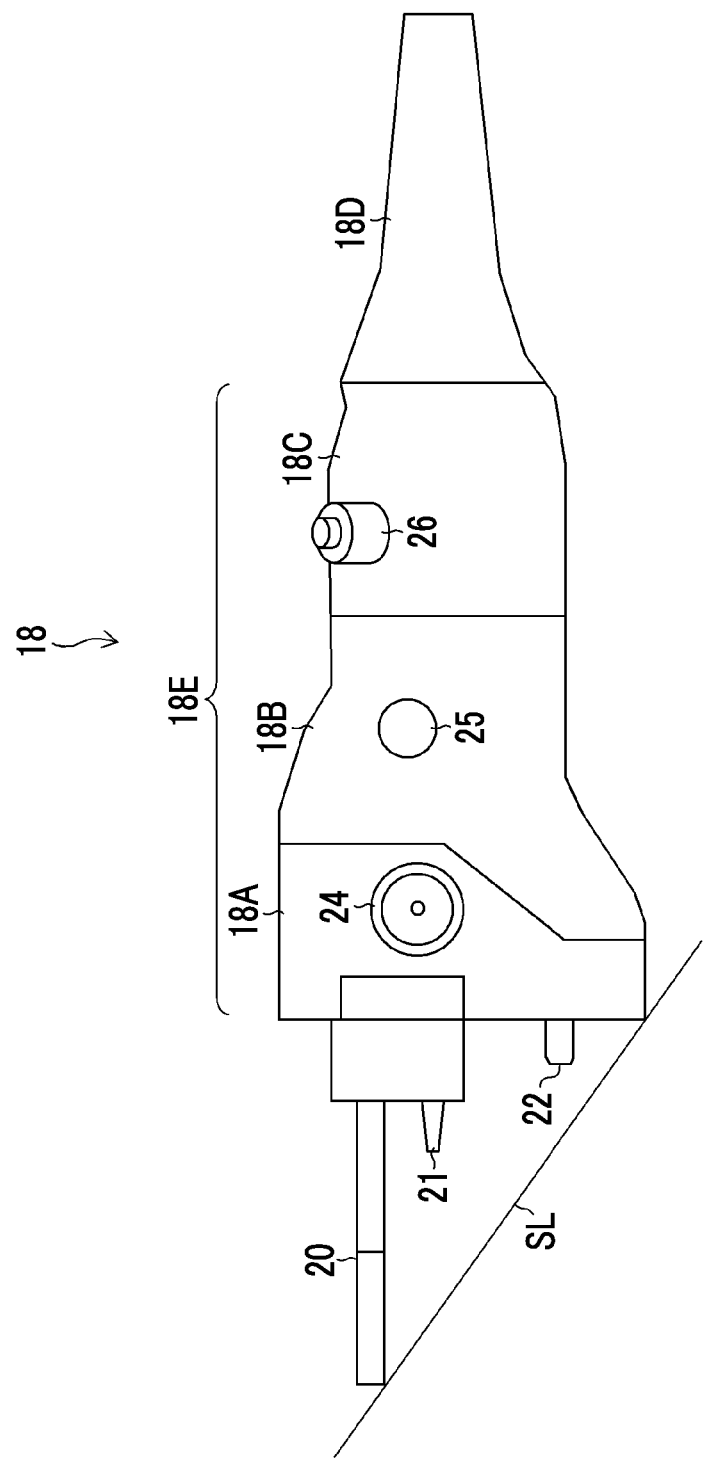
FIG. 4 is a side view of the first connector of the endoscope.

FIG. 4 is a side view of the first connector. In the present embodiment, as the positional relationship among the light guide rod 20, the shaft 22, and the exterior of the first connector 18, it is preferable that the shaft 22 is disposed on the inner side of a straight line SL connecting the light guide rod 20 and the exterior of the first connector 18 to each other. By arranging the shaft 22 on the inner side of the straight line SL connecting the distal end of the light guide rod 20 to the exterior of the first connector 18 on a side where the shaft 22 is formed, it is possible to prevent the shaft 22 from coming in contact with the floor even when the first connector 18 is dropped, for example. Therefore, it is possible to prevent the shaft 22 from being damaged.

Next, the assembling procedure of the first connector 18 of the endoscope 10 will be described with reference to FIGS. 5 to 7.

Figure 5:
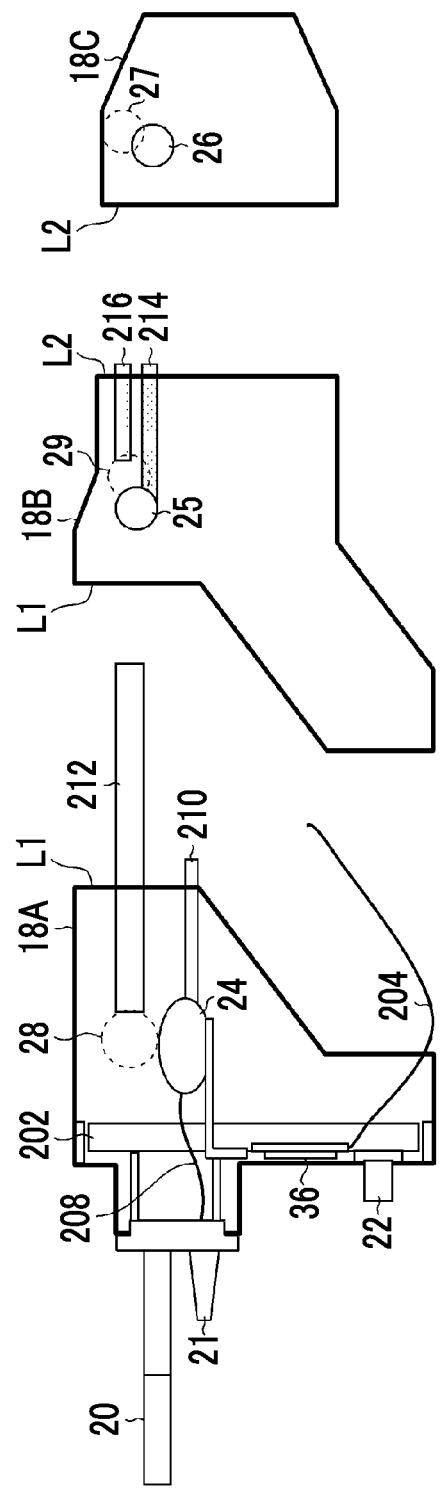
FIG. 5 is a diagram showing a part of the process of assembling the first connector of the endoscope.

As shown in FIG. 5, the first connector case 18A, the second connector case 18B, and the third connector case 18C that form the first connector body 18E are prepared. On the surface of the first connector case 18A connected to the second connector 12 of the endoscope processor device 11, the light guide rod 20, the air cap 21, and the shaft 22 are provided so as to protrude from the connection surface. In addition, the power receiving unit 36 is disposed on a side close to the connection surface in the first connector case 18A. The power receiving unit 36 is fixed to a frame 202 provided inside the first connector case 18A. Accordingly, the power receiving unit 36 is disposed in the internal space (hollow structure) of the first connector case 18A. Here, the frame 202 is a metal frame. A secondary coil can be used as the power receiving unit 36.

A cable 204 is connected to the power receiving unit 36.

An air supply conduit assembly configured to include an air supply conduit 208, the air and water supply connector 24 connected to a conduit branched from the air supply conduit 208, and an air and water supply conduit 210 formed by a water supply conduit and an air supply conduit inserted into the branch conduit is prepared. The air supply conduit assembly is attached to the first connector case 18A. The air supply conduit 208 and the air cap 21 are connected to each other. The air and water supply connector 24 is attached to the side surface of the first connector case 18A. The air and water supply connector 24 is disposed in the first connector case 18A, and the air supply conduit 208 and the air and water supply conduit 210 are disposed in the internal space (hollow structure) of the first connector case 18A.

The suction connector 28 is attached to the side surface of the first connector case 18A opposite to the air and water supply connector 24. A suction conduit 212 is attached to the suction connector 28. The suction connector 28 is disposed in the first connector case 18A, and the suction conduit 212 is disposed in the internal space (hollow structure) of the first connector case 18A.

In the present embodiment, the balloon connector 25 is attached to the side surface of the second connector case 18B. A balloon conduit 214 is attached to the balloon connector 25. The balloon conduit 214 is disposed in the internal space (hollow structure) of the second connector case 18B.

The auxiliary water supply connector 29 is attached to the side surface of the second connector case 18B opposite to the balloon connector 25. An auxiliary water supply conduit 216 is attached to the auxiliary water supply connector 29. The auxiliary water supply conduit 216 is disposed in the internal space (hollow structure) of the second connector case 18B.

In the present embodiment, the ventilation connector 26 is attached to the side surface of the third connector case 18C. The S connector 27 is attached to the side surface of the third connector case 18C opposite to the ventilation connector 26.

As described above, the first connector case 18A, the second connector case 18B, and the third connector case 18C are prepared. As shown in FIG. 5, a portion where the first connector case 18A and the second connector case 18B are in contact with each other is the division line L1, and a portion where the second connector case 18B and the third connector case 18C are in contact with each other is the division line L2.

Figure 6:
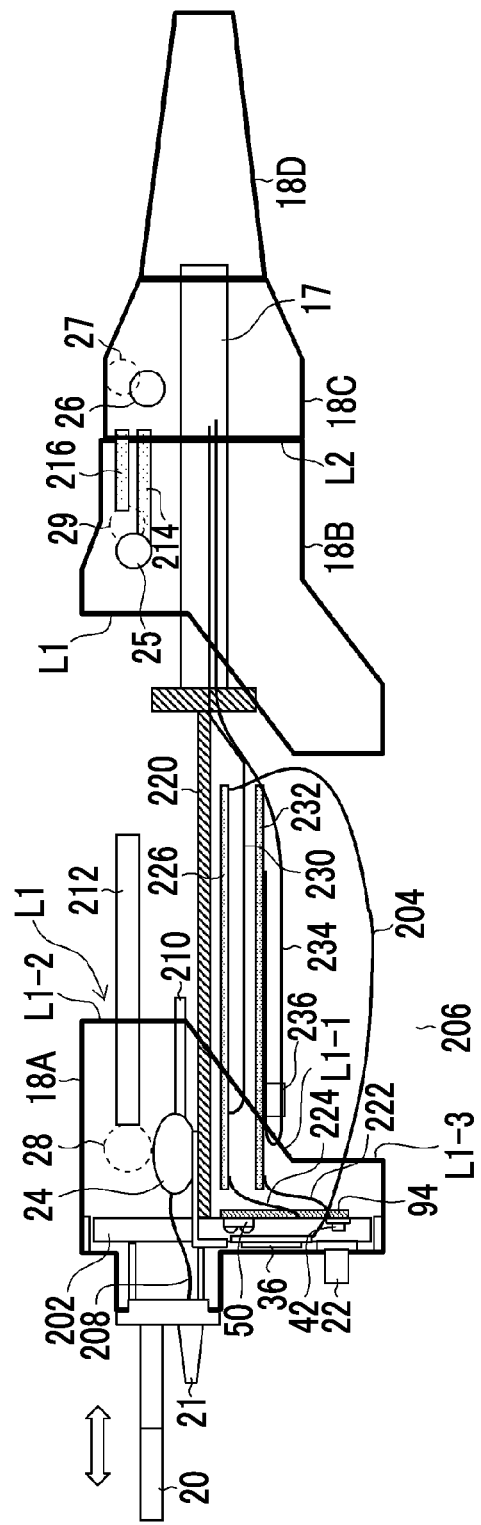
FIG. 6 is a diagram showing a part of the process of assembling the first connector of the endoscope.

Then, as shown in FIG. 6, a base frame 220 is inserted into the first connector case 18A. One end of the base frame 220 is fixed to the frame 202 disposed in the first connector case 18A. The base frame 220 is formed of a metal, for example.

The image signal transmission unit 42 and the endoscope side signal transmission and reception unit are mounted on a circuit board 94. On the circuit board 94, an image signal cable 222 electrically connected to the image signal transmission unit 42 is provided, and a control signal cable 224 electrically connected to the endoscope side signal transmission and reception unit 50 is provided. By mounting the image signal transmission unit 42 and the endoscope side signal transmission and reception unit on one circuit board 94, it is possible to reduce the number of components disposed inside the first connector 18.

The circuit board 94 is a substrate for supporting the image signal transmission unit 42 and the endoscope side signal transmission and reception unit 50, and is a substrate having wiring lines that are electrically connected to the image signal transmission unit 42 and the endoscope side signal transmission and reception unit 50. A rigid substrate, a flexible substrate, and the like can be used as the circuit board 94. By fixing the circuit board 94 to the frame 202, the image signal transmission unit 42 and the endoscope side signal transmission and reception unit 50 are disposed in the internal space (hollow structure) of the first connector case 18A. The image signal transmission unit 42 is, for example, IrDA, and the endoscope side signal transmission and reception unit 50 is a laser light emitting element. The circuit board 94 can also be divided into two separate circuit boards, which are a circuit board on which the image signal transmission unit 42 is mounted and a circuit board on which the endoscope side signal transmission and reception unit 50 is mounted.

The power receiving unit 36 is disposed so as to be closer to the second connector 12 (not shown) than the image signal transmission unit 42 and the endoscope side signal transmission and reception unit 50 are. That is, the power receiving unit 36 is disposed on the connection surface side of the first connector case 18A. By arranging the power receiving unit 36 close to the second connector 12 (not shown), efficient reception of electric power becomes possible.

In the present embodiment, as shown in FIG. 6, the division line L1 between the first connector case 18A and the second connector case 18B includes an inclined portion L1-1 that is inclined with respect to the insertion direction of the first connector 18 and the second connector 12, which is shown by the arrow, when viewed from the side surface. Here, the insertion direction of the first connector 18 and the second connector 12 is a movement direction when inserting the first connector 18 into the second connector 12, and is a direction approximately parallel to the light guide rod 20.

The air and water supply connector 24 and the suction connector 28 are disposed on one side of the first connector case 18A, and the power receiving unit 36, the image signal transmission unit 42, and the endoscope side signal transmission and reception unit 50 are disposed in the internal space (hollow structure) of the first connector case 18A on the other side thereof.

Here, the viewing from the side surface means viewing from a direction perpendicular to the insertion direction that is a direction in which the air and water supply connector 24 and the suction connector 28 located on one side and the power receiving unit 36, the image signal transmission unit 42, and the endoscope side signal transmission and reception unit 50 located in the space (hollow structure) on the other side can be recognized.

The division line L1 of the embodiment shown in FIG. 6 will be described. The air and water supply connector 24 and the suction connector 28 are formed in the first connector case 18A. That is, on the one side of the first connector case 18A, the division line L1 is located on an opposite side to the connection surface of the first connector case 18A with respect to the positions of the air and water supply connector 24 and the suction connector 28, that is, located on the universal cord 17 side.

The division line L1 includes a vertical portion L1-2 that is located from one side toward the other side and is perpendicular to the insertion direction. The division line L1 includes the inclined portion L1-1 continuous with the vertical portion L1-2. The inclined portion L1-1 is inclined with respect to the insertion direction so as to be closer to the second connector 12 (not shown) toward the other side from the one side. Although the inclined portion L1-1 is shown in a straight line in FIG. 6, the inclined portion L1-1 may have a stepwise shape, for example.

In addition, the division line L1 includes a vertical portion L1-3 that is continuous with the inclined portion L1-1 and is perpendicular to the insertion direction. Although the case has been described in which the division line L1 includes the inclined portion L1-1 and the vertical portions L1-2 and L1-3, the invention is not limited thereto. For example, the division line L1 may include only the inclined portion L1-1, or may include a plurality of inclined portions.

A circuit board 226 on which electronic devices, such as a CPU, are mounted is fixed. The circuit board 226 and the control signal cable 224 are electrically connected to each other at a location of the circuit board 226 close to the connection surface of the first connector case 18A. The circuit board 226 is used as a relay board.

The control signal cable 224 is electrically connected to the circuit board 226 in a state where the circuit board 226 and the circuit board 94 are fixed. Since the division line L1 of the first connector case 18A includes the inclined portion L1-1, the first connector case 18A has a shape that is open wide on a side close to the connection surface. As a result, it is possible to easily perform connection work since it is possible to access the control signal cable 224 and the circuit board 226.

In addition, since the control signal cable 224 is electrically connected to the circuit board 226 in a state where the circuit board 226 and the circuit board 94 are fixed, it is not necessary to make the control signal cable 224 longer than needed. That is, it is possible to perform assembly work without requiring the process for extra length.

The cable 204 is electrically connected to the circuit board 226 on a side opposite to the position connected to the control signal cable 224 in the circuit board 226.

Then, the universal cord 17 is connected to the other end of the base frame 220 in a state where the circuit board 226 is fixed. The universal cord 17 passes through the internal space (hollow structure) of the second connector case 18B, the third connector case 18C, and the cover rubber 18D.

A signal cable 230 inserted into the universal cord 17 is electrically connected to the circuit board 226. The signal cable 230 is electrically connected to the circuit board 226 at a location of the circuit board 226 close to the connection surface of the first connector case 18A. Signals for the operations of a switch, a motor, a zoom, and the like are transmitted through the signal cable 230.

Then, a circuit board 232 is fixed. Electronic devices formed by so-called programmable logic devices, such as a field programmable gate array (FPGA) circuit, are mounted on the circuit board 232. The circuit board 232 is for performing the correction of an image relevant to the variations in the characteristics of the image pick-up unit 30, such as sensitivity unevenness correction or defective pixel correction, in the endoscope 10. The circuit board 232 is used as a relay board.

The image signal cable 222 and the circuit board 232 are electrically connected to each other at a location of the circuit board 232 close to the connection surface of the first connector case 18A.

The image signal cable 222 is electrically connected to the circuit board 232 in a state where the circuit board 232 and the circuit board 94 are fixed. Since the division line L1 of the first connector case 18A includes the inclined portion L1-1, the first connector case 18A has a shape that is open wide on a side close to the connection surface. As a result, it is possible to easily perform connection work since it is possible to access the image signal cable 222 and the circuit board 232.

In addition, since the image signal cable 222 is electrically connected to the circuit board 232 in a state where the circuit board 232 and the circuit board 94 are fixed, it is not necessary to make the image signal cable 222 longer than needed. That is, it is possible to perform assembly work without requiring the process for extra length.

A signal cable 234 inserted into the universal cord 17 is electrically connected to the circuit board 232. The signal cable 234 is electrically connected to the circuit board 226 at a location of the circuit board 226 close to the connection surface of the first connector case 18A. As a result, it is possible to easily perform connection work since it is possible to access the signal cable 234 and the circuit board 232.

In addition, the signal cable 234 is made to have extra length in order to correspond to the endoscopes 10 including the insertion parts 13 having different lengths. By performing clamping with a clamp member 236 on the side of the circuit board 232 close to the connection surface of the first connector case 18A, it is possible to perform a process for extra length of the signal cable 234.

Figure 7:
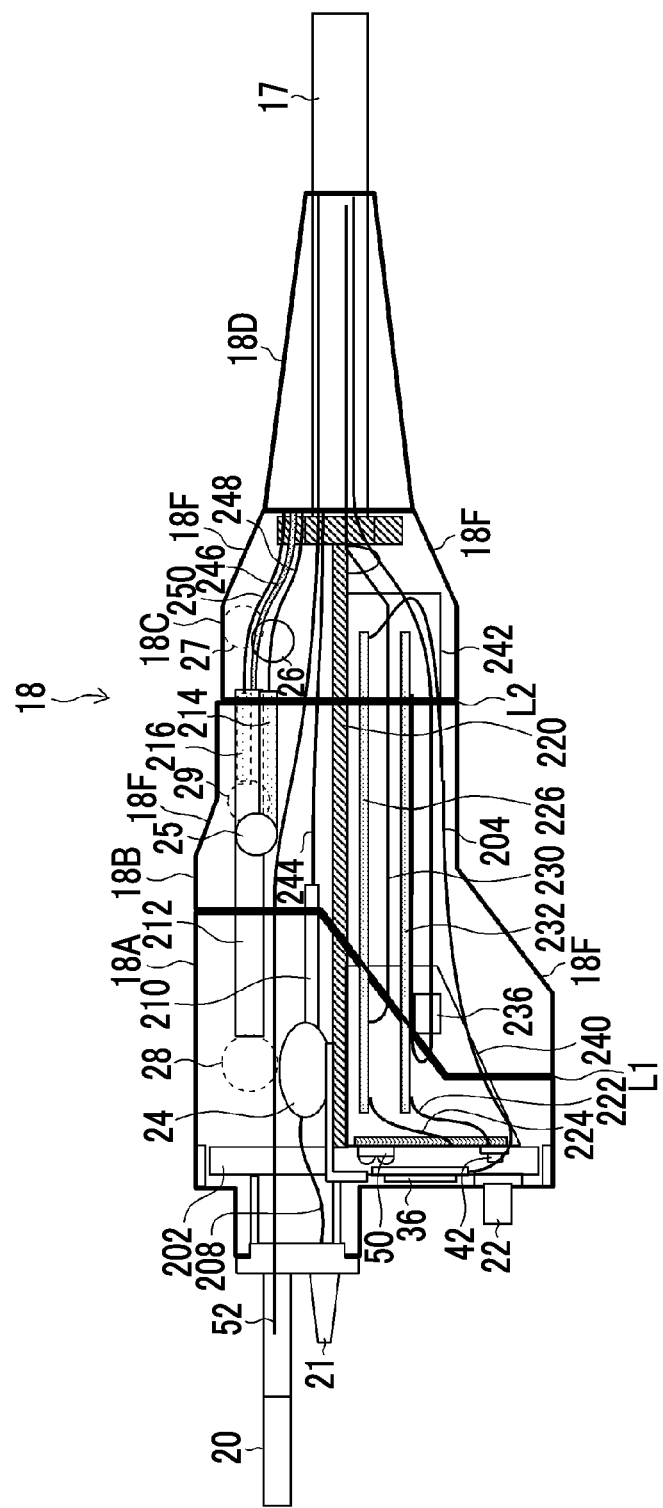
FIG. 7 is a diagram showing the first connector of the endoscope after the assembly process is completed.

Then, as shown in FIG. 7, a shield case 240 is attached so as to surround the circuit board 94, and a shield case 242 is fixed so as to surround the circuit board 232.

The light guide 52 is connected to the light guide rod 20. A tube 244 is connected to the air and water supply conduit 210, and a tube 246 is connected to the suction conduit 212.

After completing the connection within the internal space (hollow structure) of the first connector case 18A, the second connector case 18B is slid to the first connector case 18A side. The first connector case 18A and the second connector case 18B are bonded to each other.

Then, a tube 248 is connected to the balloon conduit 214, and a tube 250 is connected to the auxiliary water supply conduit 216. The second connector case 18B has a shape in which the universal cord 17 side is opened. As a result, it is possible to easily perform the work of connecting the tubes 248 and 250 since it is possible to access the balloon conduit 214 and the auxiliary water supply conduit 216.

After completing the connection within the internal space (hollow structure) of the second connector case 18B, the third connector case 18C is slid to the second connector case 18B side. The second connector case 18B and the third connector case 18C are bonded to each other. Finally, the cover rubber 18D is attached to complete the first connector 18.

In addition, repair and maintenance can be easily performed by the reverse operation of the work at the time of assembly.

As shown in FIG. 7, the first connector 18 includes a reduced diameter portion 18F toward the other side (universal cord 17 side) from the side of the second connector 12 (not shown). Here, the first connector 18 means a portion where the outer circumferential length becomes gradually shorter than that on the second connector 12 side in the reduced diameter portion 18F. In the present embodiment, each of the second connector case 18B and the third connector case 18C has the reduced diameter portion 18F. Since the first connector 18 has the reduced diameter portion 18F, the first connector 18 has a shape that the worker is likely to grip by hand.

It is preferable that the division line L1 is formed so as to be closer to the second connector than the reduced diameter portion 18F of the second connector case 18B is. That is, the division line L1 is not formed in the reduced diameter portion 18F. This is because it becomes difficult to pull out the first connector case 18A from a mold if the division line L1 is positioned in the reduced diameter portion 18F when molding the first connector case 18A using the mold.

Although the second connector case 18B includes the balloon connector 25 and the auxiliary water supply connector 29 in the present embodiment, the invention is not limited thereto. For example, in the endoscope system 2 in which the balloon connector 25 and the auxiliary water supply connector 29 are not required, the second connector case 18B may have at least one of the ventilation connector 26 and the S connector 27.

What is claimed is:

1. An endoscope, having:
an image pick-up sensor provided in a distal portion;
a light guide for transmitting light to the distal portion; and
a first connector that is connected to a second connector of an endoscope processor device and that performs electric power reception, control signal communication, and image signal communication in a non-contact manner between the endoscope and the endoscope processor device in order to drive the image pick-up sensor, wherein the first connector has a hollow structure determining an internal space and includes a power receiving unit that receives electric power from a power supply unit in a non-contact manner, an image signal transmission unit that transmits an image signal of the image pick-up sensor in a non-contact manner, and an endoscope side signal transmission and reception unit that transmits and receives a control signal for controlling the image pick-up sensor in a non-contact manner, the power receiving unit, the image signal transmission unit, and the endoscope side signal transmission and reception unit being disposed in the hollow structure,
wherein the first connector includes a first connector case and a second connector case detachable and adapted to be connected with each other to form a division line where the first and second connector cases are in contact with each other, and the division line includes an inclined portion that is inclined with respect to an insertion direction of inserting the first connector into the second connector, a first vertical portion perpendicular to the insertion direction, and a second vertical portion perpendicular to the insertion direction,
wherein an air and water supply connector and a suction connector are disposed on the first connector case and located at a first portion of the first connector case, the power receiving unit, the image signal transmission unit, and the endoscope side signal transmission and reception unit are disposed nearby a second portion of the first connector case; and a first terminal end of the inclined portion is located at the first portion and is directly connected to a terminal end of the first vertical portion, a second terminal end of the inclined portion is located at the second portion and is directly connected to a terminal end of the second vertical portion,
wherein the second vertical portion is closer to the second connector than the first vertical portion.

2. The endoscope according to claim 1,
wherein the second connector case has at least one of either an auxiliary water supply connector or a balloon connector.

3. The endoscope according to claim 2,
wherein the first connector comprises a third connector case, and the second connector case is sandwiched between the first connector case and the third connector case, and
the third connector case has at least one of either an S connector or a ventilation connector.

4. The endoscope according to claim 1,
wherein the first connector comprises a third connector case, and the second connector case is sandwiched between the first connector case and the third connector case, and
the third connector case has at least one of either an S connector or a ventilation connector.

5. The endoscope according to claim 1,
wherein the first connector has a reduced diameter portion, and a diameter of the reduced diameter portion is gradually reduced along a direction opposite to the insertion direction.

6. The endoscope according to claim 5,
wherein the division line is formed so as to be closer to the second connector than the reduced diameter portion is.

7. The endoscope according to claim 1,
wherein the power supply unit is a primary coil connected to a power source, and the power receiving unit is a secondary coil electromagnetically coupled to the primary coil.

8. The endoscope according to claim 1,
wherein the power receiving unit is disposed so as to be closer to the second connector than the image signal transmission unit and the endoscope side signal transmission and reception unit.

9. The endoscope according to claim 1, further comprising:
a circuit board on which the image signal transmission unit and the endoscope side signal transmission and reception unit are mounted.

10. An endoscope, having:
an image pick-up sensor provided in a distal portion;
a light guide for transmitting light to the distal portion; and
a first connector that is connected to a second connector of an endoscope processor device and that performs electric power reception, control signal communication, and image signal communication in a non-contact manner between the endoscope and the endoscope processor device in order to drive the image pick-up sensor, wherein the first connector has a hollow structure determining an internal space and includes a power receiving unit that receives electric powerfrom a power supply unit in a non-contact manner, an image signal transmission unit that transmits an image signal of the image pick-up sensor in a non-contact manner, and an endoscope side signal transmission and reception unit that transmits and receives a control signal for controlling the image pick-up sensor in a non-contact manner, the power receiving unit, the image signal transmission unit, and the endoscope side signal transmission and reception unit being disposed in the hollow structure,
wherein the first connector includes a first connector case and a second connector case detachable and adapted to be connected with each other to form a division line where the first and second connector cases are in contact with each other, and the division line includes an inclined portion that is inclined with respect to an insertion direction of inserting the first connector into the second connector,
wherein an air and water supply connector and a suction connector are disposed on the first connector case and located at a first portion of the first connector case; the power receiving unit, the image signal transmission unit, and the endoscope side signal transmission and reception unit are disposed nearby a second portion of the first connector case, and the inclined portion has only one straight line extending from the first portion to the second portion.

11. An endoscope, having:
an image pick-up sensor provided in a distal portion;
a light guide for transmitting light to the distal portion; and a first connector that is connected to a second connector of an endoscope processor device and that performs electric power reception, control signal communication, and image signal communication in a non-contact manner between the endoscope and the endoscope processor device in order to drive the image pick-up sensor, wherein the first connector has a hollow structure determining an internal space and includes a power receiving unit that receives electric power from a power supply unit in a non-contact manner, an image signal transmission unit that transmits an image signal of the image pick-up sensor in a non-contact manner, and an endoscope side signal transmission and reception unit that transmits and receives a control signal for controlling the image pick-up sensor in a non-contact manner, the power receiving unit, the image signal transmission unit, and the endoscope side signal transmission and reception unit being disposed in the hollow structure, wherein the first connector includes a first connector case and a second connector case detachable and adapted to be connected with each other to form a division line where the first and second connector cases are in contact with each other, and the division line includes an inclined portion that is inclined with respect to an insertion direction of inserting the first connector into the second connector, wherein a normal direction of each of the power receiving unit, the power supply unit, and the signal transmission and reception unit are parallel to an insertion direction from the first connector to the second connector.

12. An endoscope, having:

an image pick-up sensor provided in a distal portion;

a light guide for transmitting light to the distal portion; and a first connector that s connected to a second connector of an endoscope processor device and that performs electric power reception, control signal communication, and image signal communication in a non-contact manner between the endoscope and the endoscope processor device in order to drive the image pick-up sensor, wherein the first connector has a hollow structure determining an internal space and includes a power receiving unit that receives electric power from a power supply unit in a non-contact manner, an image signal transmission unit that transmits an image signal of the image pick-up sensor in a non-contact manner, and an endoscope side signal transmission and reception unit that transmits and receives a control signal for controlling the image pick-up sensor in a non-contact manner, the power receiving unit, the image signal transmission unit, and the endoscope side signal transmission and reception unit being disposed in the hollow structure, wherein the first connector includes a first connector case and a second connector case detachable and adapted to be connected with each other to form a division line where the first and second connector cases are in contact with each other, and the division line includes an inclined portion that is inclined with respect to an insertion direction of inserting the first connector into the second connector, a first vertical portion perpendicular to the insertion direction and a second vertical portion perpendicular to the insertion direction, wherein an air and water supply connector and a suction connector are disposed on the first connector case and located at a first portion of the first connector case, the power receiving unit, the image signal transmission unit, and the endoscope side signal transmission and reception unit are disposed nearby a second portion of the first connector case; and a first terminal end of the inclined portion is located at the first portion, a second terminal end of the inclined portion is located at the second portion, and the second terminal end at the second portion is closer to the second connector than the first terminal end at the first portion, wherein the first terminal end of the inclined portion is directly connected to a terminal end of the first vertical portion, the second terminal end of the inclined portion is directly connected to a terminal end of the second vertical portion, and the first vertical portion and the second vertical portion are misaligned.

* * * * *